(12) United States Patent
Rathbauer

(10) Patent No.: US 6,182,820 B1
(45) Date of Patent: Feb. 6, 2001

(54) VENEER HOLDER

(76) Inventor: John F. Rathbauer, 32 Woodbury Rd., Woodbury, NY (US) 11743

( * ) Notice: Under 35 U.S.C. 154(b), the term of this patent shall be extended for 0 days.

(21) Appl. No.: 09/183,098

(22) Filed: Oct. 30, 1998

(51) Int. Cl.$^7$ .............................. A61C 19/10; A61B 19/02
(52) U.S. Cl. .............................. 206/83; 206/63.5; 433/26
(58) Field of Search ................................ 206/63.5, 368, 206/369, 581, 564, 83, 523; 433/34, 43, 26; D24/181

(56) References Cited

U.S. PATENT DOCUMENTS

| | | | |
|---|---|---|---|
| D. 273,893 | * 5/1984 | Weitzman | D24/181 |
| 1,422,044 | 7/1922 | Edwards . | |
| 1,702,312 | 2/1929 | Pickering . | |
| 1,709,066 | * 4/1929 | Field | 206/83 X |
| 2,318,618 | 5/1943 | Myerson et al. . | |
| 2,444,294 | * 6/1948 | Jones | 206/83 |
| 2,695,112 | * 11/1954 | Bonnevay | 206/523 X |
| 2,846,725 | * 8/1958 | Tryfus | 433/26 X |
| 2,998,129 | * 8/1961 | Bekins | 206/523 |
| 3,485,344 | * 12/1969 | Aylott | 206/564 X |
| 4,180,159 | * 12/1979 | Tanaka | 206/63.5 |
| 4,226,593 | 10/1980 | Cohen et al. . | |
| 4,923,058 | * 5/1990 | Dennison | 206/83 |
| 4,991,759 | * 2/1991 | Scharf | 206/368 X |
| 5,482,464 | 1/1996 | Shimosawa et al. . | |
| 5,669,771 | 9/1997 | Lee . | |

* cited by examiner

Primary Examiner—Bryon P. Gehman
(74) Attorney, Agent, or Firm—Collard & Roe, P.C.

(57) ABSTRACT

A holder for dental implants namely dental veneers. The holder has a bottom tray and a top cover both opaque. The top cover has a recessed portion that is designed to receive a foam sheet. The foam sheet is designed to cover the top cover so that it blocks light from entering the closed holder. The bottom tray has recessed wells that are designed to receive dental veneers. When the cover is closed over the tray, the light is blocked out so that light-sensitive resin placed upon the dental veneers does not harden before the dental veneers are placed upon the patient's teeth.

10 Claims, 2 Drawing Sheets

VENEER HOLDER

BACKGROUND OF THE INVENTION

1. Field of the Invention

The invention relates to a dental veneer holder that has a bottom tray and a top cover. A dental veneer is a cap for a tooth that is applied with an adhesive. The bottom tray is a black plastic plate that has recessed wells molded into it. The top cover has a dark foam inserted into the plate to keep light from entering into the holder and to hold the veneers in place to transport them.

2. Description of the Prior Art

Many types of teeth and dental holders are known in the art. For example, U.S. Pat. No. 2,318,618 to Myerson et al. discloses a display receptacle and shipping container for artificial teeth. The manufacturer of artificial teeth mounts these teeth in properly matched sets into the receptacle. The receptacle comprises a housing that has a cap and side walls. However, this receptacle differs from the present invention because it is circular and houses false teeth, not dental veneers.

U.S. Pat. No. 1,422,044 to Edwards discloses a mount for artificial teeth comprising a sheet of cardboard or other suitable material containing a series of recesses or cavities arranged transversely across the sheet.

U.S. Pat. No. 1,702,312 to Pickering discloses a display holder for artificial teeth. The display holder includes a tray that allows a series of teeth to be mounted thereon. The tray is comprised of a tooth supporting rack that is stamped from sheet metal and in a corrugated form and shaped in a downwardly and outwardly inclined surface. The teeth are supported on these surfaces and separated by rows.

U.S. Pat. No. 5,669,771 to Lee discloses a dental restoration holder system that comprises a placement tab inserted into an oblong support. The invention also consists of a insertion tool for inserting into the placement tab. The insertion tool is used to insert dental veneers on teeth.

The prior art discloses dental holder systems that have a means for sorting teeth. However, the prior art does not disclose a dental veneer holder that has a black top cover and a black bottom tray designed to shield light from the veneers. When the dental holder is closed, the veneers are completely shielded from light. The light shielding qualities of the holder are important because they allow a light sensitive adhesive to be placed upon the dental veneers. In addition, unlike the prior art, the present invention allows the dental veneers to be arranged based upon their placement in a mouth.

SUMMARY OF THE INVENTION

These and other objects are achieved by providing a dental veneer holder that has a bottom tray and a mating top cover that are joined by a hinge. The top cover is opaque and has a recessed portion that is designed to receive a sheet of foam. The foam has a dark or opaque color and is designed to shield light from the dental veneers and to prevent veneers from shifting around during transport. The edges of the top cover and the bottom tray are designed to overlap each other so that coupled with the foam they block light from entering the holder.

The bottom tray has a series of molded recesses that are designed to receive dental veneer teeth coverings in an arrangement that is similar to their position in the patient's mouth. For example, the recessed wells are arranged in a semi-circle on the bottom tray. For example, the bottom tray has recessed wells that are in the following order: molar, $2^{nd}$ bicuspid, $1^{st}$ bicuspid, cuspid, lateral, central, central, lateral, cuspid, $1^{st}$ bicuspid, $2^{nd}$ bicuspid, molar. In this way, the dentist or dental assistant can apply these coverings to teeth quickly and efficiently.

One object of the invention is to provide a dental veneer holder that when closed shields the dental veneers from light.

Another object of the invention is to provide a dental veneer holder that has a molded recess for each tooth.

A third object of the invention is to provide a dental veneer holder that is inexpensive to manufacture and simple in design.

BRIEF DESCRIPTION OF THE DRAWINGS

Other objects and features of the present invention will become apparent from the following detailed description considered in connection with the accompanying drawings which disclose one embodiment of the present invention. It should be understood, however, that the drawings are designed for the purpose of illustration only and not as a definition of the limits of the invention.

In the drawings, wherein similar reference numerals denote similar elements throughout the several views.

DETAILED DESCRIPTION OF THE PREFERRED EMBODIMENT

Figure 1:
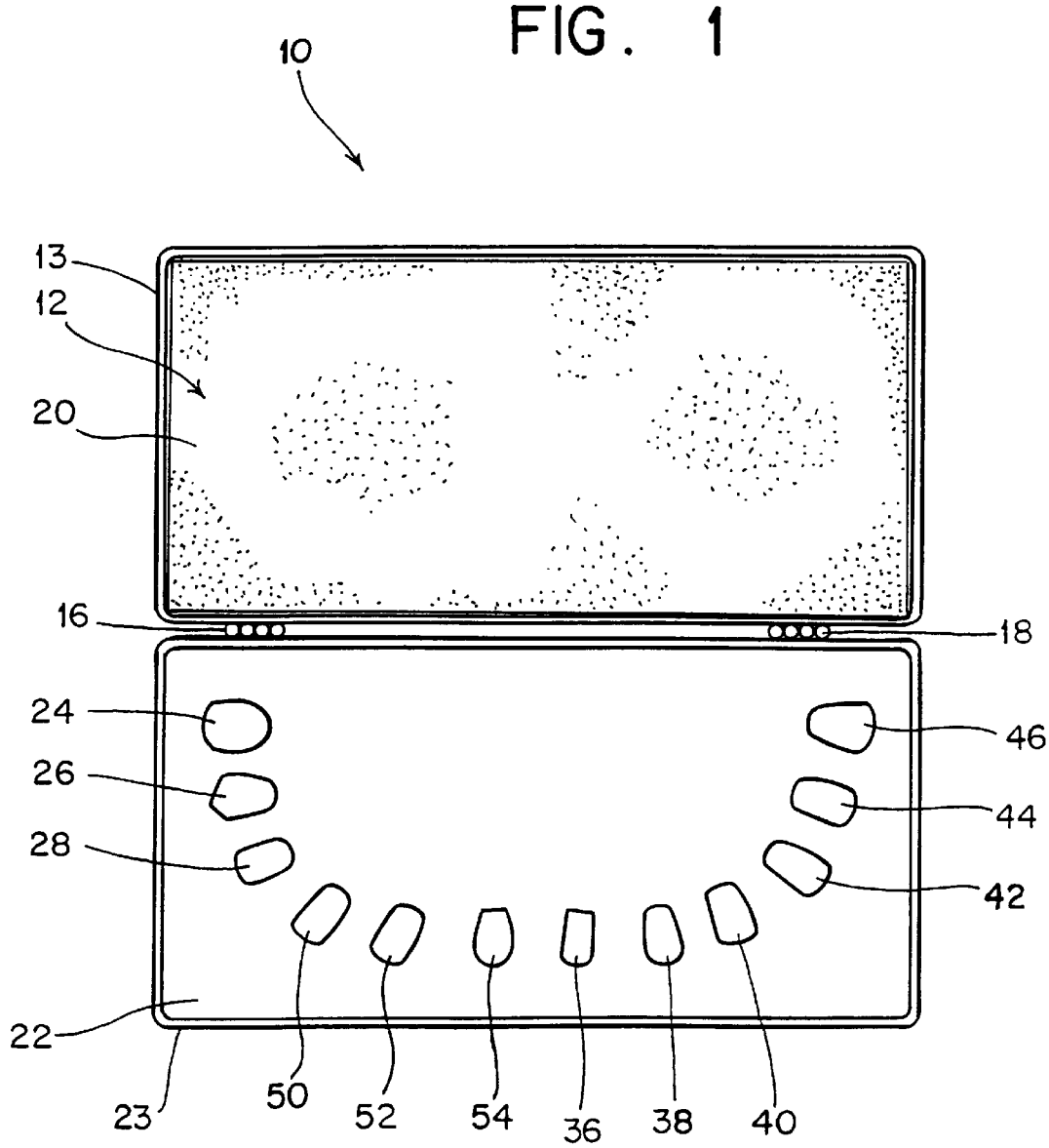
FIG. 1 is a front end view of the dental veneer holder.
Figure 2:
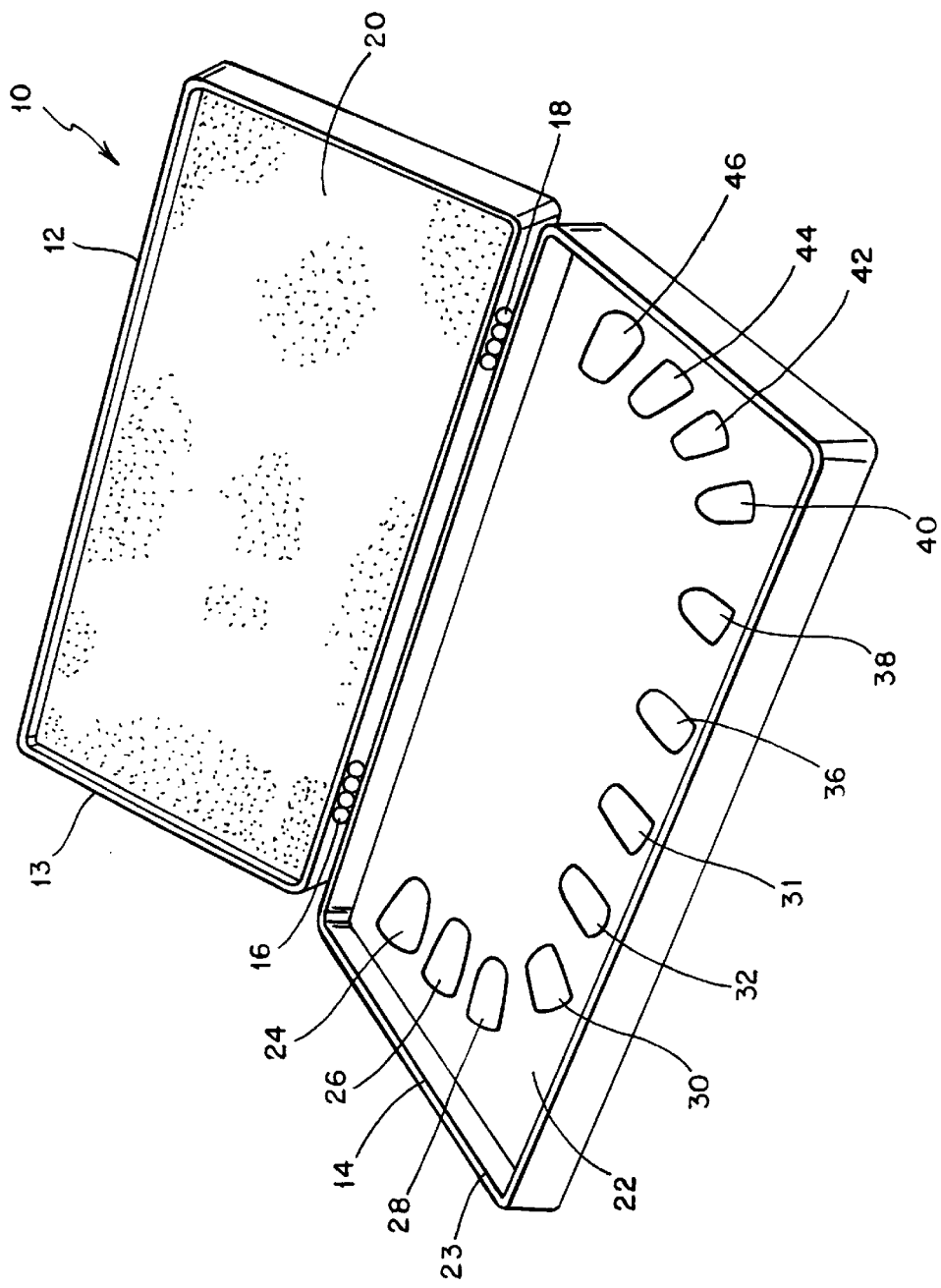
FIG. 2 is a perspective view of the dental veneer holder.

Referring to FIG. 1 there is shown a dental veneer holder 10 that has a top cover 12 having edges 13, and a bottom tray 22 having edges 23. Cover 12 and tray 22 are connected by a left hinge 16 and a right hinge 18. Inserted into top cover 12 is foam sheet 20 that is designed to fit snugly inside top cover 12. Holder 10 protects the dental veneers from light in two ways. First, cover 12 mates with tray 22 so that edges 13 on cover 12 and edges 23 on cover 22 remain flush against each other when holder 10 is closed. Second, when holder 10 is closed, foam sheet 20 blocks light from entering through cover 12 and edges 13 and 23.

A series of recessed wells are arranged on bottom tray 22 in the order of teeth in a patient's mouth. For example, there are recessed wells for dental veneers for a molar 24, a $2^{nd}$ bicuspid 26, a $1^{st}$ bicuspid 28, a cuspid 30, a lateral 32, a central incisor 34 on one side of a mouth. For the other side of the mouth, there are recessed wells for a central incisor 36, a lateral incisor 38, a cuspid 40, a $1^{st}$ bicuspid 42, a $2^{nd}$ bicuspid 44, and a molar 46.

If dental veneers are placed in holder 10, they can be stored away from the light. This fact is important because the dental veneers may be coated with a light-sensitive resin. If light hits the light-sensitive resin then the resin will harden before the dental veneers reach the teeth, thus rendering the dental veneers useless. Light-sensitive resin is placed upon the dental veneers so that when the dental veneers are placed on a person's teeth, the resin hardens causing the dental veneers to stick to the teeth.

In addition, since the dental veneers are organized and placed on the bottom tray 22 in the manner in which they appear on teeth in the mouth, this design of the bottom tray creates an organized dental veneer placement holder.

This style of dental veneer holder allows a dentist to apply the light-sensitive resin to the dental veneers and close the cover. Once the cover is closed, the dentist or dental technician can wait until the patient is ready to apply the dental veneer with the light-sensitive resin. In addition, since the dental veneer holder is organized to match a patient's mouth, the dentist does not have to waste any time applying the dental veneers to their respective teeth.

Accordingly, while only one embodiment of the present invention has been shown and described, it is to be understood that many changes and modifications may be made thereunto without departing from the spirit and scope of the invention as defined in the appended claims.

What is claimed is:

1. A dental veneer holder comprising:
   a) a top cover;
   b) a foam sheet inserted and snugly fit inside said top cover;
   c) a hinge connected to said top cover;
   d) a bottom tray connected to said hinge; and
   e) a series of recessed wells that are molded into said bottom tray wherein said series of recessed wells consist of wells that are designed to receive at least one dental veneer for each of the following teeth: a molar; a second bicuspid; a first bicuspid; a cuspid; a lateral; and a central tooth and wherein the edges of said top cover and said bottom tray are designed to overlap each other and remain flush against each other so that in combination with said foam sheet, they together block light from entering the holder at the edges.

2. The holder as in claim 1, wherein said recessed wells are arranged in a semi-circle on said bottom tray.

3. The holder as in claim 2, wherein said recessed wells are arranged to receive dental veneers in the order that they are arranged in a person's mouth.

4. The holder as in claim 3, wherein said recessed wells comprise a first recessed well that is designed to receive at least one dental veneer covering for molars.

5. The holder as in claim 4, wherein said series of recessed wells comprises twelve recessed wells.

6. The holder as in claim 1, wherein said recessed wells on said bottom tray are designed to receive at least one dental veneer covering for teeth.

7. The holder as in claim 1, wherein when said top cover is closed over said bottom tray, said holder substantially blocks light from hitting said at least one dental veneer.

8. The holder as in claim 1 wherein said bottom tray is opaque.

9. The holder as in claim 1, wherein top cover is opaque.

10. The holder as in claim 1, further comprising an opaque foam sheet fitting in between said top cover and said bottom tray on the dental veneer holder.

* * * * *